(12) United States Patent
Jones et al.

(10) Patent No.: US 9,585,695 B2
(45) Date of Patent: Mar. 7, 2017

(54) SURGICAL SCREW HOLE LINER DEVICES AND RELATED METHODS

(71) Applicant: Woven Orthopedic Technologies, LLC., Manchester, CT (US)

(72) Inventors: A. Alexander Jones, Savannah, GA (US); Anthony Viscogliosi, Manchester, CT (US)

(73) Assignee: WOVEN ORTHOPEDIC TECHNOLOGIES, LLC, Manchester, CT (US)

(*) Notice: Subject to any disclaimer, the term of this patent is extended or adjusted under 35 U.S.C. 154(b) by 0 days.

(21) Appl. No.: 14/209,518

(22) Filed: Mar. 13, 2014

(65) Prior Publication Data

US 2014/0277150 A1    Sep. 18, 2014

Related U.S. Application Data

(60) Provisional application No. 61/801,685, filed on Mar. 15, 2013, provisional application No. 61/801,778, filed on Mar. 15, 2013, provisional application No. 61/801,832, filed on Mar. 15, 2013.

(51) Int. Cl.
*A61B 17/70* (2006.01)
*A61B 17/68* (2006.01)

(52) U.S. Cl.
CPC .......... *A61B 17/686* (2013.01); *A61B 17/685* (2013.01)

(58) Field of Classification Search
CPC ................................................. A61B 17/685
See application file for complete search history.

(56) References Cited

U.S. PATENT DOCUMENTS

| | | |
|---|---|---|
| 517,668 A | 4/1894 | Still |
| 1,516,652 A | 11/1924 | Tomkinson |
| 2,326,453 A | 8/1943 | Gelpcke |
| 3,054,406 A | 9/1962 | Francis |
| 3,199,398 A | 8/1965 | Weisz |
| 3,232,163 A | 2/1966 | George |

(Continued)

FOREIGN PATENT DOCUMENTS

| | | |
|---|---|---|
| CN | 201046258 Y | 4/2008 |
| EP | 1614402 A1 | 1/2006 |

(Continued)

OTHER PUBLICATIONS

ACE Surgical Supply Co., Inc. Titanium Augmentation Micro Mesh-7, http://www.acesurgical.com/bone-grafting/graft-holding-mesh-foils/mic . . . , Jun. 19, 2014.

(Continued)

*Primary Examiner* — Ellen C Hammond
(74) *Attorney, Agent, or Firm* — Michele V. Frank; Venable LLP

(57) ABSTRACT

A sleeve system for lining a hole of a surgical screw in a bone or tissue of a subject includes a woven sleeve having a first end, a second end, and an elongated body. The elongated body has an interior portion. The first end includes an aperture that accesses the interior portion. The sleeve system also includes a protective tip that may be inserted through the aperture of the first end of the sleeve. The protective tip at least partially protects tissue of the subject from a screw positioned within the sleeve.

15 Claims, 3 Drawing Sheets

(56) References Cited

U.S. PATENT DOCUMENTS

| | | |
|---|---|---|
| 3,710,789 A | 1/1973 | Ersek |
| 3,921,496 A | 11/1975 | Helderman |
| 4,011,602 A | 3/1977 | Rybicki et al. |
| 4,064,567 A | 12/1977 | Burstein et al. |
| 4,383,527 A | 5/1983 | Asnis et al. |
| 4,409,974 A | 10/1983 | Freedland |
| 4,453,539 A | 6/1984 | Raftopoulos et al. |
| 4,566,466 A | 1/1986 | Ripple et al. |
| 4,584,722 A | 4/1986 | Levy et al. |
| 4,610,688 A | 9/1986 | Silvestrini et al. |
| 4,640,271 A | 2/1987 | Lower |
| 4,708,132 A | 11/1987 | Silvestrini |
| 4,760,843 A | 8/1988 | Fischer et al. |
| 4,790,852 A | 12/1988 | Noiles |
| 4,870,957 A | 10/1989 | Goble et al. |
| 4,894,063 A | 1/1990 | Nashef |
| 4,917,700 A | 4/1990 | Aikins |
| 5,013,318 A | 5/1991 | Spranza, III |
| 5,084,050 A | 1/1992 | Draenert |
| 5,171,148 A | 12/1992 | Wasserman et al. |
| 5,211,647 A | 5/1993 | Schmieding |
| 5,221,261 A | 6/1993 | Termin et al. |
| 5,268,001 A | 12/1993 | Nicholson et al. |
| 5,300,075 A | 4/1994 | Gordon |
| 5,354,292 A | 10/1994 | Braeuer et al. |
| 5,380,334 A | 1/1995 | Torrie et al. |
| 5,443,499 A | 8/1995 | Schmitt |
| 5,456,721 A | 10/1995 | Legrand |
| 5,458,601 A | 10/1995 | Young, Jr. et al. |
| 5,571,184 A | 11/1996 | DeSatnick |
| 5,629,077 A | 5/1997 | Turnlund et al. |
| 5,641,256 A | 6/1997 | Gundy |
| 5,713,904 A | 2/1998 | Errico et al. |
| 5,716,359 A | 2/1998 | Ojima et al. |
| 5,718,159 A | 2/1998 | Thompson |
| 5,725,541 A | 3/1998 | Anspach, III et al. |
| 5,741,325 A | 4/1998 | Chaikof et al. |
| 5,758,562 A | 6/1998 | Thompson |
| 5,766,250 A | 6/1998 | Chervitz et al. |
| 5,785,713 A | 7/1998 | Jobe |
| D397,794 S | 9/1998 | Geber |
| 5,849,013 A | 12/1998 | Whittaker et al. |
| 5,871,504 A | 2/1999 | Eaton et al. |
| 5,904,685 A | 5/1999 | Walawalker |
| 5,941,901 A | 8/1999 | Egan |
| 5,957,974 A | 9/1999 | Thompson et al. |
| 5,961,524 A | 10/1999 | Crombie |
| 5,984,926 A * | 11/1999 | Jones ............ A61B 17/686 606/309 |
| 6,019,786 A | 2/2000 | Thompson |
| 6,039,740 A | 3/2000 | Olerud |
| 6,042,592 A | 3/2000 | Schmitt |
| 6,056,751 A | 5/2000 | Fenton, Jr. |
| 6,080,155 A | 6/2000 | Michelson |
| 6,099,530 A | 8/2000 | Simonian et al. |
| 6,126,663 A | 10/2000 | Hair |
| 6,143,029 A | 11/2000 | Rippstein |
| 6,231,606 B1 | 5/2001 | Graf et al. |
| 6,241,757 B1 | 6/2001 | An et al. |
| 6,264,676 B1 | 7/2001 | Gellman et al. |
| 6,319,255 B1 | 11/2001 | Grundei et al. |
| 6,336,940 B1 | 1/2002 | Graf et al. |
| 6,342,068 B1 | 1/2002 | Thompson |
| 6,355,044 B1 | 3/2002 | Hair |
| 6,375,662 B1 | 4/2002 | Schmitt |
| 6,413,260 B1 | 7/2002 | Berrevoets et al. |
| 6,500,203 B1 | 12/2002 | Thompson et al. |
| 6,540,770 B1 | 4/2003 | Tornier et al. |
| 6,544,281 B2 | 4/2003 | ElAttrache et al. |
| 6,551,352 B2 | 4/2003 | Clerc et al. |
| 6,582,461 B1 | 6/2003 | Burmeister et al. |
| 6,616,694 B1 | 9/2003 | Hart |
| 6,645,211 B2 | 11/2003 | Magana |
| 6,669,706 B2 | 12/2003 | Schmitt et al. |
| 6,746,483 B1 | 6/2004 | Bojarski et al. |
| 6,767,350 B1 | 7/2004 | Lob |
| 6,792,979 B2 | 9/2004 | Konya et al. |
| 6,827,743 B2 | 12/2004 | Eisermann et al. |
| 6,840,769 B2 | 1/2005 | Augthun et al. |
| D503,802 S | 4/2005 | Bjarnason |
| 6,875,216 B2 | 4/2005 | Wolf |
| 6,908,466 B1 | 6/2005 | Bonutti et al. |
| 6,942,666 B2 | 9/2005 | Overaker et al. |
| 6,991,647 B2 | 1/2006 | Jadhav |
| 7,022,124 B2 | 4/2006 | Takei et al. |
| 7,052,513 B2 | 5/2006 | Thompson |
| 7,101,183 B2 | 9/2006 | Augthun et al. |
| 7,255,712 B1 | 8/2007 | Steinberg |
| 7,279,008 B2 | 10/2007 | Brown et al. |
| 7,309,355 B2 | 12/2007 | Donnelly et al. |
| 7,341,592 B1 | 3/2008 | Walters et al. |
| 7,341,601 B2 | 3/2008 | Eisermann et al. |
| 7,407,512 B2 | 8/2008 | Bojarski et al. |
| 7,513,865 B2 | 4/2009 | Bourne et al. |
| 7,547,321 B2 | 6/2009 | Silvestri et al. |
| 7,572,283 B1 | 8/2009 | Meridew |
| 7,582,108 B2 | 9/2009 | Hierlemann et al. |
| D612,499 S | 3/2010 | Ondracek et al. |
| 7,682,392 B2 | 3/2010 | Serhan et al. |
| 7,699,893 B2 | 4/2010 | Donnelly et al. |
| 7,731,750 B2 | 6/2010 | Bojarski et al. |
| 7,749,233 B2 | 7/2010 | Farr et al. |
| 7,758,642 B2 * | 7/2010 | Bojarski ............ A61B 17/0401 623/13.14 |
| 7,785,357 B2 | 8/2010 | Guan et al. |
| D626,648 S | 11/2010 | Ahlgren |
| 7,824,433 B2 | 11/2010 | Williams |
| 7,833,249 B2 | 11/2010 | Shaolian et al. |
| 7,892,203 B2 | 2/2011 | Lenker et al. |
| 7,896,901 B2 | 3/2011 | Whittaker |
| 7,963,972 B2 | 6/2011 | Foerster et al. |
| 7,967,851 B2 | 6/2011 | Bickley et al. |
| 7,988,732 B2 | 8/2011 | Bojarski et al. |
| 8,052,720 B2 | 11/2011 | Kuester et al. |
| 8,114,141 B2 | 2/2012 | Appenzeller et al. |
| 8,128,626 B2 | 3/2012 | Justin |
| 8,151,682 B2 | 4/2012 | Lilburn et al. |
| 8,162,998 B2 | 4/2012 | Schlienger et al. |
| 8,163,031 B2 * | 4/2012 | Truckai ............... A61B 17/686 623/23.51 |
| 8,202,306 B2 | 6/2012 | Dreyfuss |
| 8,221,479 B2 | 7/2012 | Glazer et al. |
| 8,226,714 B2 | 7/2012 | Beck, Jr. et al. |
| 8,226,715 B2 | 7/2012 | Hwang et al. |
| 8,241,340 B2 | 8/2012 | Froehlich |
| 8,257,395 B2 | 9/2012 | Bhatnagar et al. |
| 8,298,262 B2 | 10/2012 | Stone et al. |
| 8,308,779 B2 | 11/2012 | Reiley |
| 8,317,799 B2 | 11/2012 | Schon et al. |
| 8,317,863 B2 | 11/2012 | Cauldwell et al. |
| 8,353,941 B2 | 1/2013 | Fricker et al. |
| 8,361,078 B2 | 1/2013 | Beyar et al. |
| 8,366,711 B2 | 2/2013 | Rabiner et al. |
| 8,372,115 B2 | 2/2013 | Kohm et al. |
| 8,382,849 B2 | 2/2013 | Thomas |
| 8,420,113 B2 | 4/2013 | Zhao |
| 8,435,293 B2 | 5/2013 | Donnelly et al. |
| 8,443,706 B2 | 5/2013 | Egres, Jr. |
| 8,523,902 B2 | 9/2013 | Heaven et al. |
| 8,523,916 B2 | 9/2013 | Anderson et al. |
| 8,523,951 B2 | 9/2013 | Kania |
| 8,545,499 B2 | 10/2013 | Lozier et al. |
| 8,546,456 B2 | 10/2013 | Rose et al. |
| 8,568,413 B2 | 10/2013 | Mazur et al. |
| 8,585,762 B2 | 11/2013 | Hall |
| 8,591,582 B2 | 11/2013 | Anderson et al. |
| 8,617,185 B2 | 12/2013 | Bonutti et al. |
| 8,636,753 B2 | 1/2014 | Buevich et al. |
| 8,652,171 B2 | 2/2014 | Stone et al. |
| 8,663,296 B2 | 3/2014 | Williams |
| 8,663,672 B2 | 3/2014 | Manrique et al. |
| 8,671,815 B2 | 3/2014 | Hancock et al. |
| 8,690,962 B2 | 4/2014 | Dignam et al. |
| 8,696,748 B2 | 4/2014 | Bojarski et al. |

(56) References Cited

U.S. PATENT DOCUMENTS

| | | | |
|---|---|---|---|
| 8,709,055 B2 | 4/2014 | Beyar et al. | |
| 8,721,519 B2 | 5/2014 | Sheu et al. | |
| 8,747,470 B2 | 6/2014 | Beck, Jr. et al. | |
| 8,753,391 B2 | 6/2014 | Lu et al. | |
| 8,770,081 B2 | 7/2014 | David et al. | |
| D723,166 S | 2/2015 | Igaki et al. | |
| 8,956,394 B1 * | 2/2015 | McDonnell | A61B 17/686 606/300 |
| 8,992,537 B1 | 3/2015 | McDonnell | |
| 2002/0055749 A1 | 5/2002 | Esnouf et al. | |
| 2002/0143340 A1 | 10/2002 | Kaneko | |
| 2003/0036761 A1 | 2/2003 | Smothers et al. | |
| 2003/0045880 A1 | 3/2003 | Michelson | |
| 2004/0133204 A1 | 7/2004 | Davies | |
| 2005/0070930 A1 | 3/2005 | Kammerer | |
| 2005/0216006 A1 * | 9/2005 | Orbay | A61B 17/685 606/62 |
| 2005/0251143 A1 | 11/2005 | Dillard | |
| 2005/0255230 A1 | 11/2005 | Clerc et al. | |
| 2006/0089646 A1 | 4/2006 | Bonutti | |
| 2006/0129148 A1 | 6/2006 | Simmons et al. | |
| 2007/0060923 A1 | 3/2007 | Dreyfuss | |
| 2007/0118131 A1 | 5/2007 | Gooch | |
| 2007/0118144 A1 | 5/2007 | Truckai et al. | |
| 2007/0191956 A1 | 8/2007 | Prewett et al. | |
| 2007/0250114 A1 | 10/2007 | Drapeau | |
| 2007/0270941 A1 | 11/2007 | Headley et al. | |
| 2008/0255560 A1 | 10/2008 | Myers et al. | |
| 2008/0262630 A1 | 10/2008 | Fulmer et al. | |
| 2008/0281430 A1 | 11/2008 | Kelman et al. | |
| 2009/0024147 A1 | 1/2009 | Ralph et al. | |
| 2009/0216338 A1 | 8/2009 | Gingras et al. | |
| 2009/0279980 A1 | 11/2009 | Gruber | |
| 2009/0306777 A1 | 12/2009 | Widmer et al. | |
| 2010/0016940 A1 | 1/2010 | Shokoohi et al. | |
| 2010/0076503 A1 | 3/2010 | Beyar et al. | |
| 2010/0125273 A1 | 5/2010 | Schwieger et al. | |
| 2010/0152786 A1 | 6/2010 | Behrbalk | |
| 2010/0168505 A1 | 7/2010 | Inman et al. | |
| 2010/0179591 A1 | 7/2010 | Saltzman et al. | |
| 2010/0292738 A1 | 11/2010 | Reiley | |
| 2010/0318085 A1 | 12/2010 | Austin et al. | |
| 2010/0324607 A1 | 12/2010 | Davis | |
| 2010/0331881 A1 | 12/2010 | Hart | |
| 2011/0106177 A1 | 5/2011 | Lewis | |
| 2011/0144766 A1 | 6/2011 | Kale et al. | |
| 2011/0184472 A1 | 7/2011 | Niederberger et al. | |
| 2011/0213467 A1 | 9/2011 | Lozier et al. | |
| 2011/0230948 A1 | 9/2011 | Ehrenreich et al. | |
| 2012/0065649 A1 | 3/2012 | Towler | |
| 2012/0123416 A1 | 5/2012 | Gelfand et al. | |
| 2012/0172934 A1 | 7/2012 | Fisher et al. | |
| 2012/0239145 A1 | 9/2012 | Peterson et al. | |
| 2012/0245704 A1 | 9/2012 | Childs | |
| 2012/0259372 A1 | 10/2012 | Glazer et al. | |
| 2013/0013065 A1 | 1/2013 | Bills | |
| 2013/0014544 A1 | 1/2013 | Winkler | |
| 2013/0018318 A1 | 1/2013 | Ravichandran et al. | |
| 2013/0103166 A1 | 4/2013 | Butler et al. | |
| 2013/0131684 A1 | 5/2013 | Farrell | |
| 2013/0178946 A1 | 7/2013 | Monaghan et al. | |
| 2013/0184819 A1 | 7/2013 | Donnelly et al. | |
| 2013/0226204 A1 | 8/2013 | Kumar | |
| 2013/0289621 A1 | 10/2013 | Fulmer et al. | |
| 2014/0052178 A1 | 2/2014 | Dooney, Jr. | |
| 2014/0094805 A1 | 4/2014 | Bonutti et al. | |
| 2014/0100590 A1 | 4/2014 | Gingras et al. | |
| 2014/0128916 A1 | 5/2014 | Williams | |
| 2014/0207145 A1 | 7/2014 | Sennett | |
| 2014/0277150 A1 | 9/2014 | Jones et al. | |
| 2014/0277449 A1 | 9/2014 | Jones | |
| 2016/0038206 A1 | 2/2016 | McDonnell | |
| 2016/0074071 A1 | 3/2016 | McDonnell et al. | |
| 2016/0074072 A1 | 3/2016 | McDonnell et al. | |

FOREIGN PATENT DOCUMENTS

| | | |
|---|---|---|
| FR | 2725615 A1 | 4/1996 |
| FR | 2955259 A1 | 7/2011 |
| GB | 2 307 179 A | 5/1997 |
| WO | WO-83/02555 A1 | 8/1983 |
| WO | WO-89/01320 A1 | 2/1989 |
| WO | WO-94/07425 A1 | 4/1994 |
| WO | WO-96/03084 A1 | 2/1996 |
| WO | WO-01/56506 A1 | 8/2001 |
| WO | WO-01/70135 A2 | 9/2001 |
| WO | WO-2006/105935 A1 | 10/2006 |
| WO | WO-2007/103404 A2 | 9/2007 |
| WO | WO-2012/116319 A2 | 8/2012 |
| WO | WO-2012/121726 A1 | 9/2012 |
| WO | WO-2013/004763 A1 | 1/2013 |

OTHER PUBLICATIONS

BIOMESH® Neurological Patches N3L—Spinal dura-mater substitutes—Cousin Biotech, <http://www.cousin-biotech.com/uk/produit.php?idrubrique=16&idspecialite=35&idproduit=81>, Jun. 19, 2014.

Bioretec—ActivaScrew Cannulated—Surgical Technique, <http://www.bioretec.com/products/pro_orthotrauma/activascrew-cannulated/surgical-technique.php>, Jun. 12, 2014.

ConMed, Fixation Implants, <http://www.conmed.com/products/knee-fixation.php>, Jun. 10, 2014.

GORE-TEX® Soft Tissue Patch, <http://www.goremedical.com/stp/>, Jun. 19, 2014.

Medtronic Sofamor Danek, Vertex® Max, Reconstruction System Surgical Technique, © 2005.

The Open Prosthetics Project: suspension, <http://openprosthetics.org/suspension> Jun. 16, 2014.

Synthes GmbH, Angular Stable Locking System (ASLS). For angular stable locking of intra-medullary nails, Technique Guide, © Oct. 2008.

Synthes GmbH, DLS Dynamic Locking Screw. Combined with LCP Locking Compression Plate, Instructions for Use, © Oct. 2012.

Vicryl® (polyglactin 910) Woven Mesh—Ethicon, http://www.ethicon.com/healthcare-professionals/products/tissue-hernia/mesh/vicryl-polyglactin-910-woven-mesh , Jun. 19, 2014.

K.P. Chellamani et al., Medical textiles using Braiding Technology, Journal of Academia and Industrial Research (JAIR), vol. 2, Issue 1, Jun. 2013, pp. 21-26.

Ho Jung Kang et al., An Experimental Intraarticular Implantation of Woven Carbon Fiber Pad into Osteochondral Defect of the Femoral Condyle in Rabbit, Yonsei Medical Journal, vol. 32, No. 2, 1991, pp. 108-116.

D. S. Muckle et al., Biological Response to Woven Carbon Fibre Pads in the Knee, The Journal of Bone and Joint Surgery, 1989, 71-B, pp. 60-62.

Takanobu Nishizuka et al., Intramedullary-fixation Technique for Long Bone Fragility Fractures Using Bioabsorbable Materials, Orthopedic Research Annual Meeting, Mar. 2014.

Maureen Suchenski, M.D. et al., Material Properties and Composition of Soft-Tissue Fixation, Arthroscopy: The Journal of Arthroscopic and Related Surgery, vol. 26, No. 6, Jun. 2010, pp. 821-831.

Stephanie C. Von Plocki, et al., Biodegradable Sleeves for Metal Implants to Prevent Implant-Associated Infection: An Experimental In Vivo Study in Sheep, Veterinary Surgery, vol. 41, Issue 3, Apr. 2012, pp. 410-421.

Andre Weimann, M.D., et al., Primary Stability of Bone-Patellar Tendon-Bone Graft Fixation With Biodegradable Pins, Arthroscopy: The Journal of Arthroscopic and Related Surgery, vol. 19, No. 10, Dec. 2003, pp. 1097-1102.

McDonnell, U.S. Appl. No. 14/569,541, filed Dec. 12, 2014.

U.S. Appl. No. 29/524,091, filed Apr. 16, 2015.

International Search Report in International Application No. PCT/US15/50483, dated Dec. 28, 2015.

(56) References Cited

OTHER PUBLICATIONS

International Search Report and Written Opinion in related International Application No. PCT/US2015/050506, mailed Dec. 14, 2015.
International Search Report and Written Opinion in corresponding International Application No. PCT/US2015/065028, mailed Feb. 12, 2016.

\* cited by examiner

SURGICAL SCREW HOLE LINER DEVICES AND RELATED METHODS

CROSS-REFERENCE TO RELATED APPLICATIONS

This application claims priority to U.S. Provisional Application Nos. 61/801,685, filed Mar. 15, 2013; 61/801,778, filed Mar. 15, 2013; and 61/801,832, filed Mar. 15, 2013, the disclosures of which are incorporated herein by reference in their entirety.

TECHNICAL FIELD OF THE INVENTION

This invention generally relates to a device or method for restoring or lining the internal surface of a screw hole used with a surgical screw. More particularly, but not by way of limitation, to a suture based device and method for resurfacing and lining holes for pedicle screws.

BACKGROUND OF THE INVENTION

U.S. Pat. No. 7,758,642, which is incorporated herein in its entirety by reference, discloses the use of a perforated sheet to assist in implant fixation. U.S. Pat. No. 5,984,926, issued on Nov. 16, 1999, which is incorporated herein in its entirety by reference, discloses a suture based device for saving screw holes in bone, as well as various problems associated with achieving adequate grip or achieving adequate bone screw purchase strength in cancellous bone or osteopenic/osteoporotic bone or bone where the fractures or poor quality bone preclude optimal engagement of bone.

Because of the variety of types of injuries, bone conditions and anatomical variations and limitations, there remains a need for devices that improve screw purchase strength in a variety of clinical situations. Known methods, such as the method described in U.S. Pat. No. 8,163,031 to Truckai et al., incorporated herein in its entirety by reference, discloses a sleeve for improving the grip of the screw with the bone. However, the Truckai et al. device does not allow the surgeon to adjust the thickness of the insert. Also, a significant problem associated with pedicle screws is that they often move within the screw hole, and the sharp point of the screw causes damage to the bone around the tip, as well as causes pain to the patient due to the close proximity of the screw tip and nerves or other sensitive tissue.

Still further, the device disclosed in U.S. Pat. No. 5,984,926 may be inserted using a rod, and thus the device would benefit from the use of an insert that would assist the surgeon in engaging and centering the sleeve while pushing the sleeve into the screw hole.

BRIEF SUMMARY OF THE INVENTION

According to an embodiment of the current invention, a sleeve system for lining a hole of a surgical screw in a bone or tissue of a subject is provided. The sleeve system includes a woven sleeve having a first end, a second end, and an elongated body. The elongated body has an interior portion, and the first end includes an aperture accessing the interior portion. The sleeve system may also include a protective tip that is insertable through the aperture of the first end of the sleeve. The protective tip at least partially protects tissue of the subject from a screw positioned within the sleeve.

According to another embodiment of the current invention, a method of lining a hole for a surgical screw in a bone or tissue of a subject is provided. The method includes providing at least one woven sleeve, the at least one woven sleeve having a first end, a second end, and an elongated body with an interior portion. The first end may include an aperture accessing the interior portion. The method may also include inserting a protective tip into the aperture of the first end, and positioning the second end of the at least one woven sleeve in a desired position within the bone or tissue of the subject by pushing the protective tip with a rod. The at least one woven sleeve may be formed from a plurality of suture material.

According to another embodiment of the current invention, a sleeve system for lining a hole of a surgical screw in a bone or tissue of a subject is provided. The sleeve system includes a woven sleeve having a first end, a second end, and an elongated body with an interior portion. The first end has an aperture accessing the interior portion. The sleeve system may also include a protective cap positioned in the second end of the woven sleeve. The protective cap may at least partially protects tissue of the subject from a screw positioned within the sleeve.

A method of lining a hole for a surgical screw in a bone or tissue of a subject is provided according to some embodiments of the current invention. The method may include providing at least one woven sleeve that has a first end, a second end, and an elongated body with an interior portion. The first end may have an aperture accessing the interior portion. The method may also include providing a protective cap that fits in the second end of the at least one woven sleeve, and positioning the second end of the at least one woven sleeve in a desired position within the bone or tissue of the subject.

According to an embodiment of the current invention, a surgical screw system is provided. The surgical screw system may include a plurality of woven sleeves, each woven sleeve having a first end, a second end, and an elongated body with an interior portion. The first end may have an aperture accessing the interior portion, and the second end may be at least partially closed. At least one of the plurality of woven sleeves may be insertable into at least one other of the plurality of woven sleeves such that an outer-most sleeve of the plurality of woven sleeves is positioned in or between a bone or tissue of a subject. The surgical screw system may further include a surgical screw that is insertable within an inner-most sleeve of the plurality of woven sleeves.

According to another embodiment of the current invention, a method of implanting a surgical screw within or between a bone or tissue of a subject is provided. The method may include inserting a plurality of woven sleeves into the bone or tissue of the subject. Each of the plurality of woven sleeves may have a first end, a second end, and an elongated body with an interior portion. The first end may have an aperture accessing the interior portion, and the second end may be at least partially closed, a first woven sleeve of the plurality of woven sleeves being inserted into or between the bone or tissue of the subject, and one or more subsequent woven sleeves of the plurality of woven sleeves being inserted into the interior portion of an immediately-preceding woven sleeve of the plurality of woven sleeves to be inserted. The method may also include inserting the surgical screw within the inner most sleeve of the plurality of woven sleeves.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE INVENTION

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. All references cited in this specification are incorporated herein by reference.

Figure 1A:
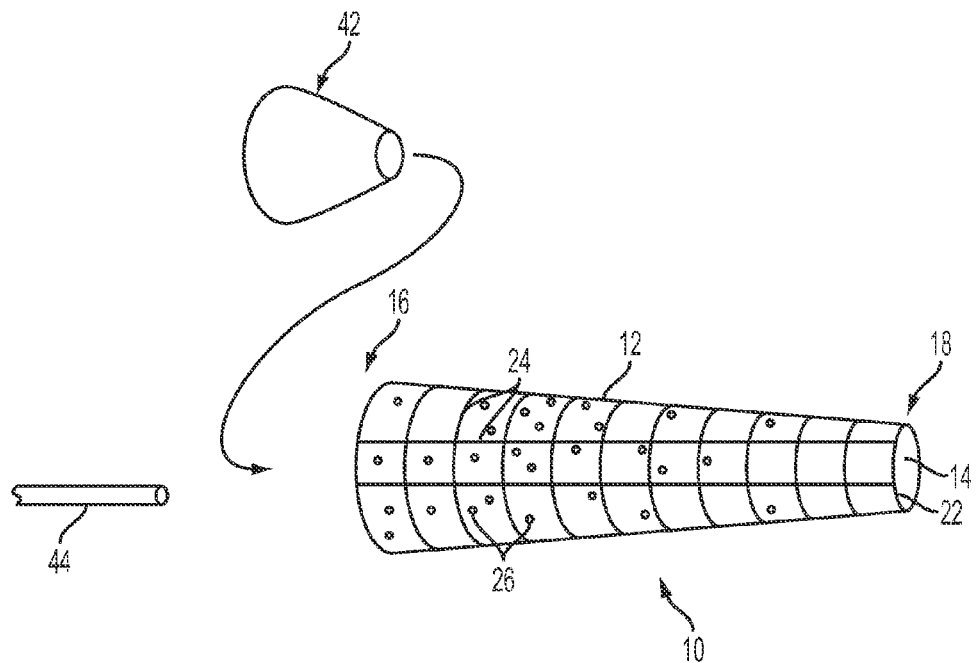
FIG. 1A shows an example of a screw sleeve with a protective nipple according to an embodiment of the present invention.
Figure 1B:
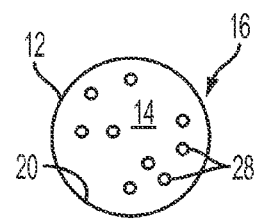
FIG. 1B shows a cross-section of a first end of the screw sleeve shown in FIG. 1A according to an embodiment of the present invention.

A sleeve device and system used to create support for surgical screws and prosthetic devices according to an embodiment of the present invention is shown in FIG. 1A. FIG. 1A shows a woven sleeve 10 with an elongated body 12 having an interior portion 14. The body includes a first end 16 and second end 18. The first end 16 includes an aperture 20 that provides access to the interior portion 14 of the woven sleeve 10 (see FIG. 1B). The second end 18 of the woven sleeve 10 may be closed or at least partially closed. For example, at least a portion of the body 12 can be tapered such that the second end 18 is closed or partially closed.

As shown in FIG. 1A, the sleeve system may include a protective tip 42, or nipple. The protective tip 42 can be insertable into the first end 16 of the sleeve 10. A rod 44 may also be included. The rod 44 may be used to push the protective tip 42 through the body 12 of the sleeve 10 to, for example, the second end 18 of the sleeve 10. In addition, the sleeve 10 may itself be pushed into a desired location within a bone or tissue of a subject by the force of the rod 44 pushing the protective tip 42. The protective tip 42 may provide a surface to be engaged and pushed by the rod 44. This rod 44 and protective tip 42 may also facilitate centering of the sleeve 10 within the bone or tissue of the subject, based on, at least in part, the shape of the protective tip 42, as well as the shape of the sleeve 10. The protective tip 42 may also be used to protect the fibers or suture material 24 from the threads and/or sharp tip of a screw inserted to the sleeve. Additionally, the protective tip 42 may protect the surrounding tissue from the threads and/or tip of the screw.

Figure 2:
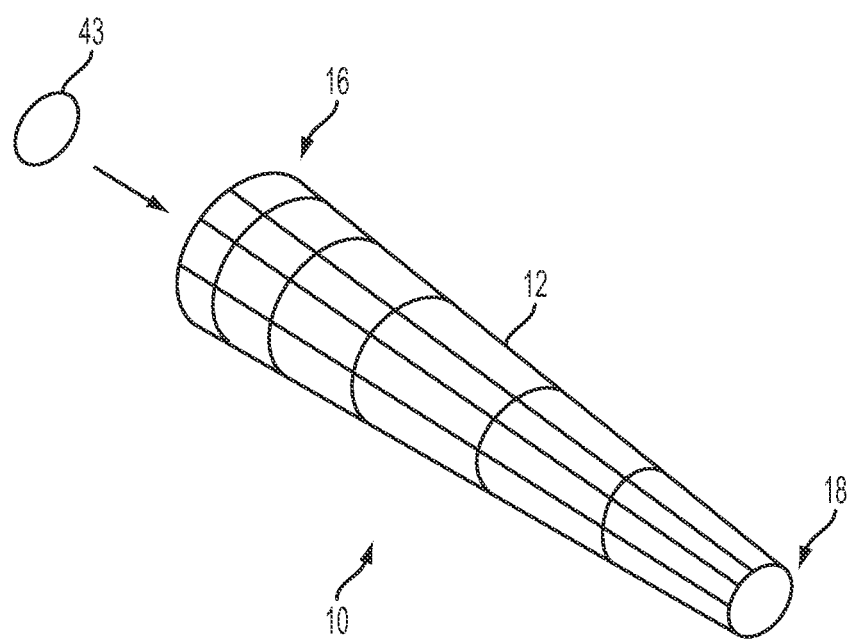
FIG. 2 shows an example of a screw sleeve with a protective cap according to an embodiment of the present invention.

FIG. 2 shows an embodiment of the invention that includes a protective cap 43 that is insertable through the aperture 20 of the first end 16 of the sleeve 10. Alternatively, the protective cap 43 may affixed to or integral with the second end 18 of the sleeve 10. The protective cap 43 may be fixed to the first end 16 by adhesive or by being molded to the suture material 24 of the sleeve 10. In another embodiment, the cap 43 may be integral with the second end 18 of the sleeve 10, or insertable through the first end 16 and subsequently positioned in the second end 18 of the sleeve 10. The cap 43 may protect the fibers or suture material 24 from the threads of a screw, which might otherwise cut or damage the fibers or suture material 24 of the sleeve 10 when the screw is inserted into the sleeve 10. Additionally, the cap 43 may protect surrounding tissue from the sharp tip of the screw.

Figure 3:
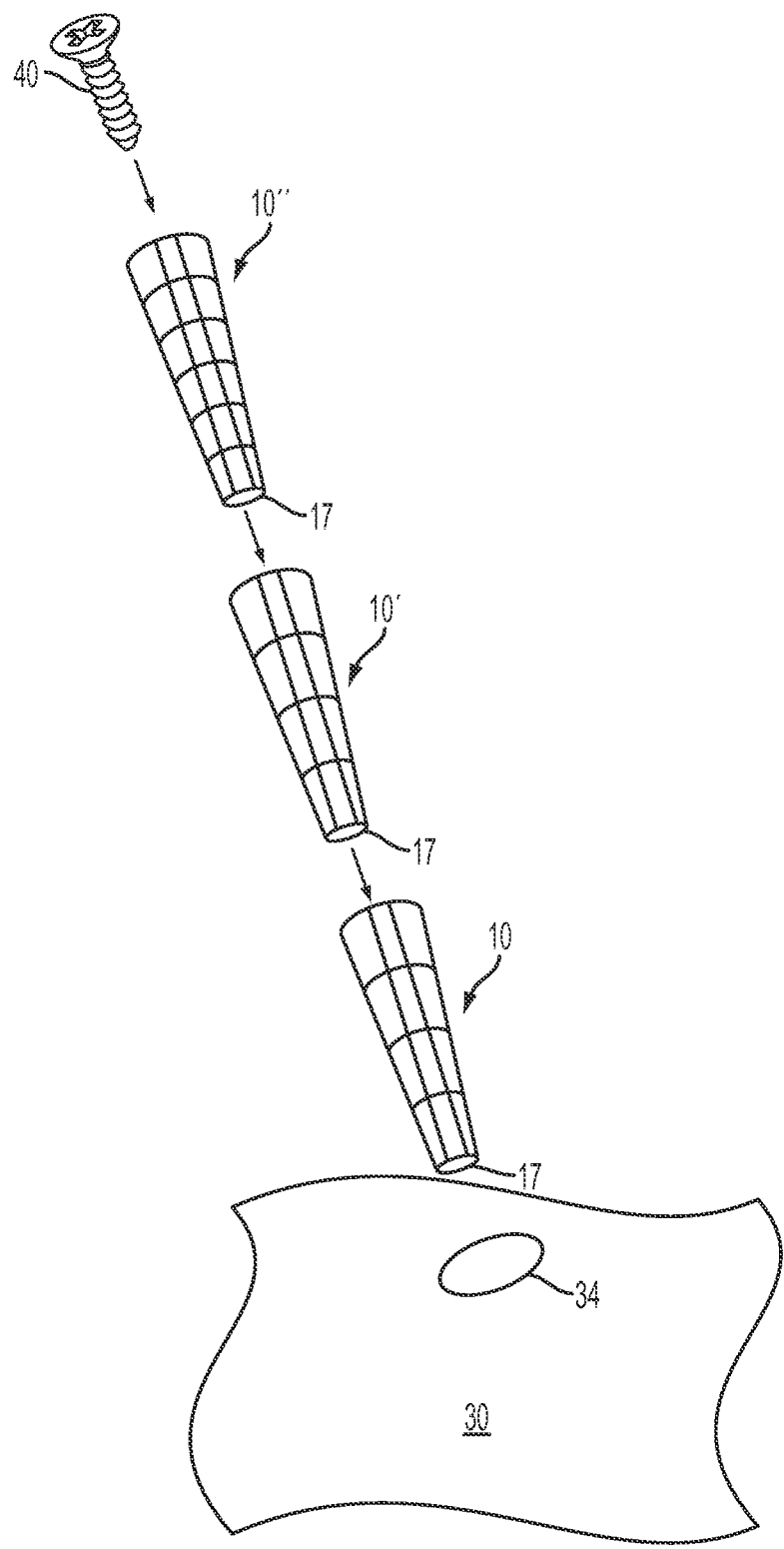
FIG. 3 shows an example of a multi-sleeve screw sleeve according to an embodiment of the present invention.

FIG. 3 shows a screw sleeve system according to another embodiment of the present invention. According to this embodiment, multiple sleeves 10, 10', 10" are provided for inserting into a bone or tissue of the subject. Although three sleeves 10, 10', 10" are shown in FIG. 3, embodiments are not limited to three sleeves, and more or fewer sleeves can be provided. Sleeve 10 can be inserted into a bone 30 or tissue by being pushed through a hole 34 formed in the bone 30, for example. Sleeve 10' can then be inserted into sleeve 10. Similarly, sleeve 10" can be inserted into sleeve 10'. Accordingly, in the example shown in FIG. 3, three sleeves 10, 10', 10" will be nested within each other when placed in the desired position within bone 30. Screw 40 may then be positioned within sleeve 10". The multi-sleeve arrangement can enhance the purchase or grip of the screw 40 and protect or shield the patient from the sharp tip of the screw 40. Each of the sleeves 10, 10', 10" in FIG. 3 has a closed end 17. Alternatively, one or more of the sleeves 10, 10', 10" may have an open end in place of closed end 17. Additionally, a protective tip 42 or cap 43 may be used in one or more of sleeves 10, 10', 10".

A screw (see screw 40 in FIG. 3) or other surgical securing means may be inserted within the space 14 of the sleeve 10, 10', or 10" in any of the above embodiments, and thereby placed and firmly held within a bone or tissue of the subject.

According to some embodiments, the sleeve 10 may be impregnated with a suitable adhesive or bone cement 26, as shown in FIG. 1, to add thickness to the sleeve and rigidity to the assembly when cured. For example, the adhesive or bone cement 26 can be impregnated into the woven structure of the sleeve 10 before implanting into the bone or tissue of a subject, and can remain uncured until placed in the desired position. Alternatively, the bone cement or adhesive 26 can be added to or impregnated into the sleeve 10 in situ. In some embodiments, the bone cement or adhesive 26 is added after the sleeve is implanted into the subject. The body 12 of the sleeve 10 may be woven from a plurality of components 24, such as, for example, suture material. However, the sleeve 10 may also be woven from other threads, fibers, or materials suitable for use in the body of a patient. Additionally, the woven sleeve 10 may be filled with one or more of various materials 28, including a morselized bone graft, a bone growth-stimulating agent, such as a bone morphogenic protein (BMP), and/or an antibiotic agent to provide protection against infection. The woven sleeve may also, or alternatively, be filled with an uncured adhesive or bone cement, which can be in liquid or gel form, for example.

According to embodiments of the present invention, the sleeve 10 is able to be placed or inserted, for example, into an area within or surrounding an open fracture in a bone 30 or within a bone 30 (see FIG. 3). A hole 34 may be created in a bone 32 for accepting the sleeve 10. After being delivered to the desired location on, against, or within a bone or between two sections of bone, the sleeve 10 may solidify and integrate with surrounding bone and tissue, which can be aided, at least in part, by bone cement or adhesive 26 and/or materials 28.

According to the above descriptions and related drawings, embodiments of the present invention can include, for example, the following features.

According to one embodiment, a sleeve system for lining a hole of a surgical screw in a bone or tissue of a subject is provided. The sleeve system includes a woven sleeve 10 having a first end 16, a second end 18, and an elongated body 12 with an interior portion 14, the first end 16 having an aperture 20 that accesses the interior portion 14. The sleeve system may also include a nipple or protective tip 42 that is insertable through the aperture 20 of the first end 16 of the sleeve 10. The protective tip 42 can at least partially protect tissue of the subject from a screw 40 positioned within the sleeve 10. The protective tip may have a conical or frusto-conical shape, for example.

The second end 18 of the sleeve 10 may be at least partially closed relative to the first end 16. For example, the second end 18 may have an aperture 22 that is smaller than the aperture 20 of the first end 16, or no aperture. The sleeve 10 may be formed of a plurality of suture material 24 that is woven or interconnected.

The sleeve system may further include a rod 44. During use, the rod 44 can be inserted through the aperture 20 of the first end 16 to push the protective tip 42 down the elongated body 12 of the sleeve 10. The protective tip 42 and sleeve 10 may be configured such that the protective tip 42 moves the sleeve 10 into a desired position when the protective tip 42 is pushed by the rod 44. Additionally, the sleeve system may further include at least one additional woven sleeve 10', 10" that can be inserted into the woven sleeve 10 when the woven sleeve 10 is positioned within the bone or tissue of the subject. The surgical screw may then be inserted into a last sleeve 10" of the at least one additional woven sleeve to be inserted into the woven sleeve 10.

According to an embodiment, a method of lining a hole for a surgical screw in a bone or tissue of a subject is provided. The method includes providing at least one woven sleeve 10, whose features are consistent with the above-described embodiments, inserting a protective tip 42 into the aperture 20 of the first end 16, and positioning the second end 18 of the at least one woven sleeve 10 in a desired position within the bone or tissue of the subject by pushing the protective tip 42 with a rod 44. The method may also include positioning an inner woven sleeve 10', 10" of the at least one woven sleeve within another sleeve of the at least one woven sleeve by using the rod 44 to push the protective tip 42 within the inner woven sleeve 10.

According to an embodiment, a sleeve system for lining a hole of a surgical screw in a bone or tissue of a subject includes a woven sleeve, and a protective cap 43 positioned in the second end 18 of the woven sleeve 10. The protective cap 43 may at least partially protect tissue of the subject from a screw 40 positioned within the sleeve 10. In some embodiments, the protective cap 43 may be fixed to the second end 18 by adhesive. Alternatively, or additionally, the protective cap 43 may be molded to the suture material 24 in the second end 18 of the woven sleeve 10.

A method of lining a hole for a surgical screw in a bone or tissue of a subject, according to another embodiment, includes providing at least one woven sleeve 10, providing a protective cap 43 configured to fit in the second end 18 of the at least one woven sleeve 10, and positioning the second end 18 of the at least one woven sleeve 10 in a desired position within the bone or tissue of the subject. The protective cap 43 may be integral with the second end 18 of the at least one woven sleeve 10.

According to another embodiment, a surgical screw system includes a plurality of woven sleeves 10, 10', 10", each having a construction corresponding to the above-described woven sleeves. At least one of the plurality of woven sleeves 10, 10', 10" being configured to be inserted into at least one other of the plurality of woven sleeves such that an outer-most sleeve 10 of the plurality of woven sleeves is positioned in or between a bone or tissue of a subject. The system also may include a surgical screw 40 to be inserted within an inner-most sleeve 10" of the plurality of woven sleeves.

According to an embodiment of the present invention, a method of implanting a surgical screw within or between a bone or tissue of a subject includes inserting a plurality of woven sleeves into the bone or tissue of the subject, a first woven sleeve of the plurality of woven sleeves being inserted into or between the bone or tissue of the subject, and one or more subsequent woven sleeves being inserted into the interior portion of an immediately-preceding woven sleeve of the plurality of woven sleeves to be inserted (see FIG. 3). The method may also include inserting the surgical screw within the inner more sleeve 10" of the plurality of woven sleeves.

According to an embodiment of the present invention, it has been discovered that the problems left unanswered by known art can be solved by providing a method for creating support for surgical screws and prosthetic devices. The method includes creating a screw hole for a pedicle screw and providing a woven sleeve. The woven sleeve has an elongated body with a first end, a second end, and an interior portion. The first end has an aperture allowing access to the interior portion of the woven sleeve. The woven sleeve may be formed from a plurality of suture material and the second end of the woven sleeve may be closed or at least partially closed. The method may further include providing a generally conical or frusto-conical tip that is insertable into the first end of the sleeve. The method may also include inserting the woven sleeve into the screw hole, and then inserting the pedicle screw through the sleeve to its designed depth of use such that the tip of the pedicle screw abuts the plastic tip when it reaches the designed depth of use.

According to some embodiments, a second woven sleeve, or several woven sleeves, may be inserted into the hole for the pedicle screw before inserting the pedicle screw. The positioning of the sleeves in the hole prior to the insertion of the pedicle screw will enhance the purchase or grip of the pedicle screw and protect or shield the patient from the sharp tip of the pedicle screw. Thus, the disclosed invention will allow the screw to develop enhanced grip, while providing the additional benefits of a shield that protects the patient from gouging by the sharp edges of the tip of the pedicle screw.

According to another embodiment, a method for creating support for surgical screws and prosthetic device is provided. The method includes creating a screw hole for a pedicle screw and providing a woven sleeve with an elongated body having a first end, a second end, and an interior portion. The first end includes an aperture allowing access to the interior portion of the woven sleeve. The woven sleeve may be formed from a plurality of suture material and the second end of the woven sleeve may be at least partially closed. The method may also include inserting the woven sleeve into the screw hole, and then inserting the pedicle screw through the sleeve to its designed depth of use such that the tip of the pedicle screw abuts the plastic tip when it reaches the designed depth of use.

According to an embodiment of the present invention, a method of lining a hole for a pedicle screw is provided. The method includes providing one or more woven sleeves, each sleeve having an elongated body that includes a first end, a second end, and an interior portion. The first end includes an aperture allowing access to the interior portion of the woven sleeve. The second end of the woven sleeve being closed or partially closed. The woven sleeve may be formed from a plurality of suture material. A conical or frusto-conical tip may be provided that is insertable into the first end of one of the sleeves. The method may further include placing the conical or frusto-conical tip into the first sleeve to be inserted into the screw hole, and inserting the second end of the sleeve into the screw hold by pushing against the conical or frusto-conical tip. The method may also include inserting one or more additional sleeves into one or more sleeves that have been inserted into the screw hole with the aid of the conical or frusto-conical tip. Additionally, the method may include inserting the pedicle screw into the center-most sleeve.

According to another embodiment of the present invention, a method of lining a hole for a pedicle screw includes providing several woven sleeves, each sleeve with an elongated body having a first end, a second end, and an interior portion. The first end may have an aperture allowing access to the interior portion of the woven sleeve, and the second end of the woven sleeve being closed. The woven sleeve may be formed from a plurality of suture material. A protective cap may be nested into the second end and preferably fixed to the second end by adhesive or by molded into the suture material. The method may also include inserting the pedicle screw into the center-most sleeve.

According to another embodiment of the present invention, a method of lining a hole for a pedicle screw includes providing several woven sleeves, each sleeve with an elongated body having a first end, a second end, and an interior portion. The first end may have an aperture allowing access to the interior portion of the woven sleeve, and the woven sleeve may be formed from a plurality of suture material. The second end of the woven sleeve may be closed. The method may also include inserting the pedicle screw into the center-most sleeve.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A sleeve system for lining a hole of a surgical screw in a bone or tissue of a subject, comprising:
    a woven sleeve having a first end, a second end, and an elongated body with an interior portion, the first end having an aperture accessing the interior portion;
    at least one additional woven sleeve configured to be inserted into the woven sleeve when the woven sleeve is positioned within the bone or tissue of the subject; and
    a protective tip configured to be positioned in the second end of the woven sleeve within the bone via insertion through the aperture of the first end of the woven sleeve or the at least one additional woven sleeve.

2. The sleeve system according to claim 1, wherein the second end is at least partially closed relative to the first end.

3. The sleeve system according to claim 1, wherein the sleeve is formed of a plurality of suture material that is woven or interconnected.

4. The sleeve system according to claim 1, further comprising a rod configured to be inserted through the aperture of the first end and to push the protective tip into the elongated body of the sleeve.

5. The sleeve system according to claim 1, wherein the protective tip and sleeve are configured such that the protective tip moves the sleeve into a desired position when the protective tip is pushed by a rod.

6. The sleeve system according to claim 1, wherein the at least one additional woven sleeve is configured so that a surgical screw can be inserted into the at least one additional woven sleeve.

7. The sleeve system according to claim 1, wherein the protective tip has a conical or frusto-conical shape.

8. The sleeve system according to claim 1, wherein the protective tip is configured to at least partially protect tissue of the subject from a screw positioned within the sleeve.

9. The sleeve system according to claim 1, wherein the at least one additional woven sleeve is configured, when inserted into the woven sleeve within the bone or tissue, to be held in direct contact with the woven sleeve.

10. A sleeve system for lining a hole of a surgical screw in a bone or tissue of a subject, comprising:
    a plurality of woven sleeves, each woven sleeve having a first end, a second end, and an elongated body with an interior portion, the first end having an aperture accessing the interior portion; and
    a protective cap configured for positioning in the second end of at least one of the plurality of woven sleeves,
    wherein the plurality of woven sleeves are configured to nest within each other when disposed within the bone or tissue of the subject, and
    wherein the protective cap is configured to at least partially protect tissue of the subject from a screw positioned within at least one of the plurality of sleeves.

11. The sleeve system according to claim 10, wherein the protective cap is fixed to the second end by adhesive.

12. The sleeve system according to claim 10, wherein the woven sleeve comprises a plurality of suture material that is woven or interconnected.

13. The sleeve system according to claim 12, wherein the protective cap is fixed to the second end by being molded to the suture material in the second end of the woven sleeve.

14. The sleeve system according to claim 10, further comprising a surgical screw configured to be inserted within an inner-most sleeve of the plurality of woven sleeves.

15. The sleeve system according to claim 10, wherein the plurality of woven sleeves are configured such that each of the plurality of woven sleeves, when nested within each other when disposed within the bone or tissue, is held in direct contact with at least one other of the plurality of woven sleeves.

* * * * *